United States Patent
Agrawal et al.

(10) Patent No.: US 8,687,189 B2
(45) Date of Patent: Apr. 1, 2014

(54) ANALYSIS OF ARRAYS BY LASER INDUCED BREAKDOWN SPECTROSCOPY

(75) Inventors: Anoop Agrawal, Tucson, AZ (US); Juan Carlos L. Tonazzi, Tucson, AZ (US)

(73) Assignee: Ajjer, LLC, Tucson, AZ (US)

(*) Notice: Subject to any disclaimer, the term of this patent is extended or adjusted under 35 U.S.C. 154(b) by 691 days.

(21) Appl. No.: 12/393,926

(22) Filed: Feb. 26, 2009

(65) Prior Publication Data
US 2009/0290151 A1 Nov. 26, 2009

Related U.S. Application Data

(60) Provisional application No. 61/033,157, filed on Mar. 3, 2008.

(51) Int. Cl.
*G01J 3/30* (2006.01)

(52) U.S. Cl.
USPC ............................................. 356/318

(58) Field of Classification Search
USPC ................................. 356/318, 246
See application file for complete search history.

(56) References Cited

U.S. PATENT DOCUMENTS

| | | | |
|---|---|---|---|
| 4,220,414 A * | 9/1980 | Barringer | 356/318 |
| 4,925,307 A | 5/1990 | Cremers et al. | |
| 5,041,266 A * | 8/1991 | Fox | 422/552 |
| 5,700,637 A | 12/1997 | Southern | |
| 5,744,305 A | 4/1998 | Fodor et al. | |
| 6,002,478 A * | 12/1999 | Zhu | 356/316 |
| 6,008,897 A | 12/1999 | Sabsabi et al. | |
| 6,741,345 B2 | 5/2004 | Sabsabi et al. | |
| 6,762,835 B2 | 7/2004 | Zhang et al. | |
| 7,129,093 B2 | 10/2006 | McCleskey et al. | |
| 7,195,872 B2 | 3/2007 | Agrawal et al. | |
| 2001/0034063 A1 * | 10/2001 | Saunders et al. | 436/2 |
| 2002/0093653 A1 | 7/2002 | Detalle et al. | |
| 2003/0027129 A1 | 2/2003 | Warner et al. | |
| 2004/0189990 A1 * | 9/2004 | Shilling | 356/318 |
| 2004/0235059 A1 | 11/2004 | Warner et al. | |
| 2005/0011818 A1 | 1/2005 | Warner et al. | |
| 2005/0214847 A1 | 9/2005 | Havrilla et al. | |
| 2005/0280816 A1 | 12/2005 | Agrawal et al. | |
| 2008/0220441 A1 | 9/2008 | Birnbaum et al. | |
| 2009/0046832 A1 | 2/2009 | Birnbaum et al. | |

FOREIGN PATENT DOCUMENTS

| | | |
|---|---|---|
| WO | WO2004029586 | 4/2004 |
| WO | WO2004029586 A1 | 4/2004 |
| WO | WO2008130737 | 10/2008 |
| WO | WO2008130737 A1 | 10/2008 |

OTHER PUBLICATIONS

U.S. Appl. No. 12/338,724, filed Dec. 18, 2008, Agrawal et al.
Ziegler, BL et al. "Generation of Infectious Retrovirus Aerosol Through Medical Laser Irradiation". Lasers in Surgery and Medicine. vol. 22. p. 37. 1998.

(Continued)

*Primary Examiner* — Kara E Geisel

(57) ABSTRACT

The present invention relates to the detection of materials using laser induced breakdown spectroscopy (LIBS). This invention discloses methods to draw the analyte of interest in a homogeneous matrix and subsequent analysis of these matrices, wherein the said matrices are preferably arranged in an array format. This invention is particularly applicable to analysis of Liquid samples arranged in an array format.

11 Claims, 6 Drawing Sheets

(56) References Cited

OTHER PUBLICATIONS

Wachter et al. Applied Spectroscopy. vol. 41(6). p. 1042. 1987.
Arca et al. Applied Spectroscopy. vol. 51(8). p. 1102. 1997.
Berman et al. Applied Spectroscopy. vol. 52(3). p. 438. 1998.
Chen Z. et al. "Analysis of heavy metals in liquids using Laser Induced Breakdown Spectroscopy by liquid-to-solid matrix conversion". Spectrochimica. Acta. Part B. vol. 63. p. 64. 2008.
Yaroshchyk, P. et al. "Quanitative analysis of wear metals in engine oil using LIBS: The use of paper substrates and comparison between single and double pulse LIBS". Spectrochimica Acta. Part B. vol. 60. p. 1482. 2005.
Dockery, C.R. "Speciation of chromium via laser induced breakdown spectroscopy of ion exchanged polymer membranes". Applied Spectroscopy. vol. 59. p. 252. 2005.
Zhang, H. et al. "Recyclable Hydrophilic—Hydrophobic Micropatterns on Glass for Microarray Applications". Langmuir. 23(9) pp. 4728-4731. 2007.
Keartoll B., et al. Laser induced breakdown. Spectroscopy, Sparkling new applications. Nature Photonics. vol. 2, p. 537. 2008.
American Society for Testing Materials, Test Method—D7202.
Arca et al., App Spectro, vol. 51. 1997.
Berman, et al., Applied Spectros, vol. 52. 1998.
Chen, Spectrochimica Acta, 2008.
Diaz Pace et al., Spectrochimica Acta, 2006.
Dockery, Applied Spectroscopy, 2005.
Environmental Protection Agency, USA, Test Method SW846 3050.
Environmental Protection Agency, USA, Test Method SW846 3051.
Kearton, Nature Photonics. 2008.
National Institute of Occupational Safety and Health, USA, Analytical Method 7102.
National Institute of Occupational Safety and Health, USA, Analytical Method 7300.
National Institute of Occupational Safety and Health, USA, Analytical Method 7301.
National Institute of Occupational Safety and Health, USA, Analytical Method 7303.
National Institute of Occupational Safety and Health, USA, Analytical Method 7704.
National Institute of Occupational Safety and Health, USA, Analytical Method 9102.
National Institute of Occupational Safety and Health, USA, Analytical Method 9110.
Occupational Safety and Health Administration, USA, Test Method ID 206.
Occupational Safety and Health Administration, USA, Test Method ID 121.
Occupational Safety and Health Administration, USA, Test Method ID 125g.
Wachter, et al., Appl Spectros, vol. 41. 1987.
Yaroshchyk, LIBS, Spectrochimica Acta. 2005.
Zeigler et al. Lasers in Surgery. 1998.
Zhang H., et al., Langmuir. 2007.

\* cited by examiner

Figure 1

Top View

Front view

ANALYSIS OF ARRAYS BY LASER INDUCED BREAKDOWN SPECTROSCOPY

RELATED APPLICATION/CLAIM OF PRIORITY

This application is related to and claims priority from provisional application Ser. No. 61/033,157 filed on Mar. 3, 2008, which provisional application is incorporated by reference herein.

FIELD OF THE INVENTION

The present invention relates to the detection of contaminants in environmental and industrial hygiene samples using laser induced breakdown spectroscopy (LIBS). This method can be used to analyze biological materials, industrial, industrial hygiene and environmental samples of soil, air, water, surfaces and any others for contamination by metals and their compounds. The method is specifically aimed at arrays of samples formed by analytes that have been extracted in a homogenous matrix.

BACKGROUND OF THE INVENTION

Environmental and industrial hygiene samples originate from air, water, soil and surfaces from places such as, industrial sites, waste storage, dumps and those that may have been contaminated by other human and natural activities. Some of the toxic industrial materials are lead, hexavalent chromium, cadmium, mercury and beryllium to name a few prominent ones. These materials are typically analyzed by extracting the toxin or the contaminant in a liquid medium (using acids, bases and other solvents and solutions) and then subjecting this to analysis. The liquid extraction ensures that the samples are captured in a homogenous matrix. Typical analysis involves taking these samples and analyzing them sequentially through chromatography (e.g., high performance liquid or gas chromatography), inductively coupled plasma along with atomic emission or a mass spectrometer (ICP-AES and ICP-MS respectively). All the samples to be analyzed are eluted into the equipment in a sequence with enough gap or purge so that there is no cross-contamination. To decrease the labor content and increase the efficiency of the analysis, autosamplers have been developed for such instruments. In these, the samples are put in a queue and are automatically analyzed one after the other. As an example in modern ICP-MS instruments, 200 samples may be queued which can take 10 hours to analyze. The long analysis time not only limits the throughput, but can cause drift in baseline, and for proper quantification it is customary to run calibration standards periodically, which means more sample preparation and more delay in getting the results. Laser induced breakdown spectroscopy (LIBS) is being used increasingly to look at elemental composition and molecular bonds. The core analytical aspect of this technique for elemental analysis is similar to the widely used atomic emission spectroscopy. In this technique the sample is subjected to a laser beam pulse where some of the sample is ablated, and the emission from the plasma of the ablated product is recorded and analyzed. LIBS is typically used on samples directly, without sample preparation procedures. However, for quantitative analysis this can be difficult and time consuming if the analyte of interest is not present homogenously within the sample. This invention allows one to utilize the advantages of fast analysis by LIBS on analytes by extracting them in a homogenous matrix.

The techniques developed in biological analysis lend themselves to high throughput analysis. In these methods the high throughput is obtained in two ways, first by analyzing arrays of samples (solids or liquids) where the analyte of interest is present homogenously in the sample or each array element, and second by automating the sample preparation. As an example, microarray and microwell formats are routinely used for biological samples and are then analyzed by optical scanners (by looking for fluorescence, luminescence and absorption/transmission changes and quantifying these). Typical microwell formats have 24, 96, 384, 1536 or more wells in an area of about 8 cm×13 cm. Such plates can be read by the optical scanners in a matter of minutes. Solid microarrays may have thousands of analytical spots on a plate. Further, standards may occupy some of the spots or wells of these plates so that they are all read almost simultaneously (within minutes) avoiding temporal drift.

In addition to read the samples rapidly, it is preferable to automate the sample preparation procedures which require repetitive steps of mixing various liquids, filtration, pipetting, and weighing. The purpose of this invention is to enable high throughput analysis of sample arrays that can be analyzed by LIBS.

One object of this invention is to analyze liquid samples by LIBS.

Another object of this invention is to extract the analytes of interest from a sample into a homogenous matrix, and subject arrays formed from the said matrices to analysis by LIBS.

Yet another object of the present invention is to demonstrate that environmental and industrial hygiene sample arrays can be measured at high throughputs using LIBS.

Another objective of this invention is to enable processes so that environmental and industrial hygiene sample arrays could be prepared with high degree of automation which are ready for analysis by LIBS.

Yet another objective is to be able to make multiwall arrays for compositional analysis.

SUMMARY OF THE INVENTION

In accordance with the purposes of the present invention, as embodied and broadly described herein, the present invention provides a method of analysis of liquid samples by LIBS. In particular, sample arrays are analyzed by LIBS for achieving high throughputs. For those samples where the material of interest is present heterogeneously, one extracts the sample in a homogeneous matrix and then analyzed by LIBS. Preparation of sample arrays for analysis is also disclosed.

BRIEF DESCRIPTION OF THE DRAWINGS

FIG. 1: Schematics of a 96 well plate array;
FIG. 2: Schematics of automation for sample preparation for beryllium analysis by fluorescence.

DETAILED DESCRIPTION

Figure 2A:
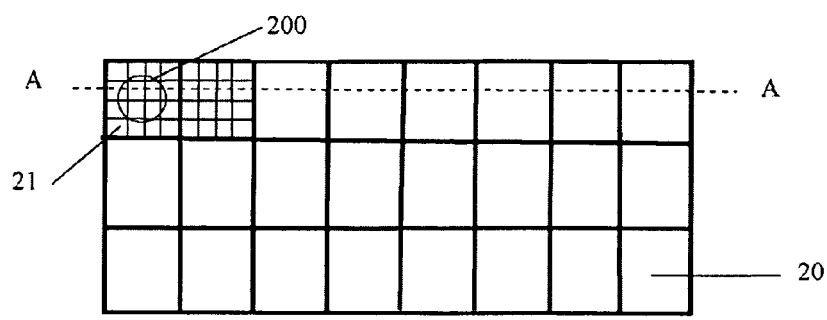
FIG. 2a: Top view of a textured microwell plate.

This invention is related to overcoming obstacles in novel ways to use laser induced breakdown spectroscopy (LIBS) to analyze samples at a high throughput, particularly environmental toxins. In this method the sample is subjected to a laser where the laser energy is absorbed in the sample which results in its ablation and formation of a plasma. The characteristic emission from the materials is measured by a spectrometer. Although the typical emissions are measured in a wavelength range of 200 to 1,000 nm, one may also use near Infra-red and Raman spectrometers for the spectra analysis. This technique has several alternative names in the literature, some of which are laser induced plasma spectroscopy, laser induced spectral emission analysis, laser spark spectroscopy, laser induced shockwave plasma spectroscopy and laser plasma spectroscopy. For this spectroscopy the most common laser system used is a pulsed Nd:YAG for which the native wavelength is 1064 nm or its second, third and fourth harmonics. The pulse energy is generally in the range of 10 µJ to about 500 mJ and the pulse duration is about 100 fs to about 200 ns.

In this invention, the sample of interest is drawn into a homogeneous medium and then arrays of such samples are analyzed. Since the homogeneous medium is typically a liquid, analysis of liquid arrays is to be undertaken. Analysis of liquids is difficult as the laser pulse dumps a large amount of energy which sends a shock wave and splatters the liquid, which interferes with the physical observation of the emission and can also cross contaminate the next sample in the array that is located nearby and contaminate the sample chamber. In addition, to get to the analytical limits one may have to analyze the same array element several times by repeated laser pulses and average the spectra. With splatter, the liquid levels can change and may take long to establish meniscus equilibrium. Thus, as disclosed in this innovation each array element is further portioned into small volumes so that the shock wave is not effectively transferred through these partitions. One can use partitioning which ranges from several microns down to nanometer scale. The energy from shock wave has alternative modes to dissipate such as viscoelastic deformation of the partitioning medium, increased friction or drag between the liquid and partitioning medium due to availability of more surface area.

To illustrate the importance of this innovation we can focus the discussion on one of the environmental toxins which is anthropogenic beryllium and its oxide. Beryllium is used as a metal, a metallic alloy and as an oxide (bulk ceramic or a coating). It has many applications in industries including electronics, aerospace, defense, and the Department of Energy (DOE) complexes. Exposure to anthropogenically formed beryllium particles can lead to a lung disease called Chronic Beryllium Disease (CBD). Recent regulations from DOE dictate a permissible exposure limit of particles to 0.2 µg/m$^3$ in air, a housekeeping level of 3 µg/100 cm$^2$ on a surface, and a release level for materials after beryllium exposure where the surface contamination due to beryllium must not exceed 0.2 µg/100 cm$^2$. LIBS is being used as a rapid technique that does not require extensive sample preparation for looking at many elements including beryllium. However, as discussed below, in its present form of use it is not desirable for many applications related to industrial hygiene or heterogeneous samples.

The popular method for detecting beryllium on a surface involves wiping an area with a wipe, performing a digestion with acid to dissolute beryllium or its compounds into a homogenous liquid matrix, and then analyzing this matrix by inductively coupled plasma (ICP) atomic emission spectroscopy (ICP-AES) or mass spectroscopy (ICP-MS). For analyzing airborne samples, one draws a known quantity of air through a solid filtering medium and then the filter is treated in a similar fashion as the surface wipes, and then analyzing the liquid in which beryllium is extracted. The ICP-AES technique requires large samples (typically 5 to 15 ml of solution). If a sample is identified as positive for beryllium or any other toxin then it is difficult to verify with a second run, as most (or all) of the sample may have been consumed in the first run. However, a more significant downside is the instrument time taken for analyzing the samples. For air filters one typically analyzes a filter after an eight hour shift to look at the total exposure in the work shift. In order to protect workers from large instantaneous release of beryllium, the sampling frequency has to be increased which places a greater burden on laboratories using traditional methods due to limited throughput.

Currently, thousands of surface wipes and air filters are analyzed annually for beryllium. It is desirable to develop techniques that can analyze contaminants on surfaces, in air and soil directly without sample preparation. However, limitations in sampling homogeneity limits this exercise. For example, when a toxin is present in air, typically its exposure to a human is determined by the total amount of toxin inhaled over a period of time (or volume of air breathed). Thus, most of the industrial hygiene sampling require that certain volume of air be collected or passed through a medium for sufficient length of time to capture toxins so as to establish an average level during this period. It is also likely that the toxin may be present in a small section of a large work area and the human exposure occurs as a person crosses through this area. For these reasons, many of the workers are required to carry personnel badges (which are battery powered pumps fitted with filters), and throughout their work day the air is sampled to capture the toxin if any, on the filter. The filter from this badge is then analyzed once a shift or more frequently, depending on the exposure and the toxin. Similarly, in surface sampling rather than to find a particle and then quantify, one wipes over a large area such as 100 sq cm or any other area, capture particles and then analyzes these wipes for the toxins. Such media (wipes and filters) are heterogeneous as the particles of the toxin are distributed randomly in a non-homogenous fashion. These samples and soils contaminated with particles are difficult to analyze by LIBS for quantitative information as a laser only focuses on a small area. In order to illustrate this point more clearly an example is provided on analysis of beryllium oxide particulates.

According to the DOE regulations described earlier, if on a wipe the mass of Be exceeds 0.2 µg/100 sq cm, then one has to take an action. As seen in Table 1, one 100 micron sized BeO particle in an area of 100 sq cm would put one over this regulation limit. Thus if one such particle was present on a wipe, scanning an entire wipe with a focused laser for this particle will be difficult and time consuming. Further, even if the laser zapped this particle it will be difficult to ablate a 100 micron particle completely with one pulse using the typical laser energies employed in LIBS analysis. Thus quantification of the amount of beryllium under these circumstances will be highly challenging. The same argument can be made for an air filter where one or a few such particles may be trapped which will be difficult to locate and analyze fully for beryllium content. A more effective method would be to extract all of the beryllium oxide in a homogenous matrix and then to analyze the matrix (or a fraction thereof). Typically the homogeneous medium for extraction is a liquid, which for most metallic impurities and their compounds is an acid (usually pH lower than 6). The resulting homogeneous liquid matrix may be analyzed or used to create a homogeneous solid matrix, e.g., by evaporation of the liquid, to obtain a homogenous solid which can be analyzed for beryllium content.

TABLE 1

Size of BeO particles vs amount of beryllium

| Particle size (Diameter, cm) | Particle size, diameter, μm | Volume, cc | beryllium oxide mass, μg | beryllium mass, μg |
|---|---|---|---|---|
| 0.005 | 50 | 6.55E−08 | 0.20 | 0.070686 |
| 0.01 | 100 | 5.24E−07 | 1.57 | 0.565488 |
| 0.02 | 200 | 4.19E−06 | 12.57 | 4.523904 |
| 0.1 | 1000 | 5.24E−04 | 1570.8 | 565.488 |

Thus, it can be appreciated that it is important to extract the sample from a media in an homogenous matrix to obtain reliable assessment of the analyte. Homogeneity (in the liquid or a solid) in the context of this invention means that the amount of the material of interest is well represented within the laser ablation area or volume.

LIBS instruments have been quite effective in specific cases, such as looking at compositions in process flow, monitoring of stacks from industrial waste, mapping of contamination in remote places (e.g., bore wells), spot checking (vast areas of water and soils without sample preparation), compositions of homogenous solids or liquids. As an example LIBS has been used to look at surfaces where contaminants from air or liquid are captured on a media and then a laser is used to search the surface of this media (e.g., see US patent application 2004/0189990). However, this method suffers from the limitations discussed above for quantitative analysis for non-homogenous samples.

The present invention recognizes the limitation of the LIBS, and overcomes this by analyzing samples after the analyte is extracted in a homogenous matrix, and capitalizes on the technique's advantage of rapid analysis. The analyte itself is first captured on filters or wipes. Some of the methods to capture the toxins are provided in American Society of Testing Materials (ASTM, Conshohocken, Pa.)) methods such as D1356, D5337, D6966, D7144, D7296 and E1792, D7035, D4547, D4700, D6640. Similar methods are also available from various governmental agencies that have jurisdiction in various areas, such as National Institute of Occupational Health and Safety (NIOSH, Cincinnati, Ohio), Environmental Protection Agency (EPA, Washington D.C.) and Occupational Safety and Health Administration (OSHA, Washington D.C.).

Laser-induced breakdown spectroscopy (LIBS) is mainly based on atomic emission spectroscopy (AES) which uses a highly energetic laser pulse as the excitation source. Since all elements release characteristic optical emissions when excited to a plasma state at sufficiently high temperatures, this method can detect all elements, limited only by the power of the laser as well as the sensitivity and wavelength range of detector and spectrometer resolution. Detection in LIBS and data manipulation is very similar to atomic emission spectroscopy where the samples are placed in a flame and the characteristic spectra emitted by various elements is recorded and then analyzed. The prior art on LIBS is reviewed briefly, particularly for the analysis of liquids, so as to bring out some of the specific features in LIBS technology that will be useful for this invention.

LIBS operates by focusing the laser onto a small area at the surface of the specimen; when the laser is discharged it ablates a very small amount of material, in the range of nanograms to picograms, which instantaneously generates a plasma plume with temperatures of about 10,000-20,000 K. At these temperatures, the ablated material dissociates (breaks down) into excited ionic and atomic species. During this time, the plasma emits a continuum of radiation which does not contain any useful information about the species present, but within a very small timeframe the plasma expands at supersonic velocities and cools. At this point the characteristic atomic emission lines of the elements can be observed. The delay between the emission of continuum radiation and characteristic radiation is in the order of few Us and this is why it is necessary to temporally gate the detector. Several types of lasers may be used, such as ArF, KrF, pulsed argon or krypton lasers, copper vapor lasers, carbon dioxide lasers, Ti: sapphire lasers, vertical-external-cavity-surface-emitting lasers, chromium doped ZnSe lasers, etc., but the most widely used laser for this application is Nd:YAG laser. For analyzing liquids one of the most important issue is control of splatter that is caused by the interaction of a liquid with a laser pulse and sends a shock wave through the liquid volume. This creates a mess in the sample chamber, but can also contaminate other nearby samples, such as in a closely spaced array (i.e. array element boundaries within about 5 cm of each other, e.g. see Ziegler, B. L., et al., Generation of Infectious Retrovirus Aerosol Through Medical Laser Irradiation, Lasers in Surgery and Medicine, Volume 22, p-37 (1998)). Some of the past work on liquids will be described before disclosing the novelty of the innovation. The methods used in the past can be used simultaneously with the current innovation to obtain additional enhancements to the analytical capabilities.

There are several descriptions in the prior art of analysis of liquids by LIBS. Wachter, et al (Wachter, J. R., Cremers, D. A., Applied Spectroscopy, vol 41(6), 1987, p-1042) demonstrate the analysis of a liquid in a clear vial. The detection of the spectra is done perpendicular to the laser that is impinged on the sample for excitation. When the first laser pulse (from a Q switched Nd:YAG laser) touches the liquid surface (an aqueous nitric acid solution with uranium) a large splattering was seen in the vessel, but these splatterings are reduced for the subsequent pulses as long as the time interval between these pulses is controlled. The characteristic emission is thus measured after the splattering is reduced from the first or subsequent few pulses. The pulse frequency of the excitation laser that was found to give good results within the geometric constraints of the experiment (e.g., vessel size, vessel shape, liquid volume) was about 10 Hz, with laser pulse energy of about 260 mJ with a pulse time of 15 ns. Another important aspect was the focal length of the lens used to focus the laser on to the liquid. As an example, when the focal lengths of 25, 50 and 100 mm were chosen, the distance over which the energy was sufficient to ablate the liquid and form the plasma was 0.7, 2.3 and 4 mm in depth within the liquid. In the invention that is being described here such parameters are important, because the laser should be able to focus on to the small volume of liquid in the arrays formed using microwell plates without preferably exciting the container parts, and also containing the splash.

Arca et al (Arca, G. et al, Applied Spectroscopy, vol 51(8), 1997, p-1102) also analyzed aqueous samples for trace contamination by several elements, using a Nd:YAG laser with a focusing lens of 30 cm to only perturb the surface of the liquid, and then captured the plasma using a fiber optic spectrometer and using quartz fibers to ensure high transmission of the signals at all wavelengths of interest. They measured each sample 10 times at intervals of 1 s each and showed that chromium can be determined down to 100 ppb in water and have also conducted measurements for lead and copper. They found that after the laser struck the sample a time delay of about 1 μs was required for the brehmsstrahlung emission to decrease before the characteristic line emission spectra for the elements appeared. This time delay was not dependent on the elements present in the solution.

Berman et al (Berman L. M., Wolf, P. J., Applied Spectroscopy, vol 52(3), 1998, p-438) looked into determining elemental and organic contaminants in water. 10 cm focal length lens was used with pulse energies of 60 mJ at a repetition rate of 5 to 20 Hz. When 1064 nm laser wavelength was used, the splashing of the fluid was severe. However, when they tripled the laser frequency and irradiated the sample at a wavelength of 355 nm, this was reduced. The laser was focused on the surface for best results. If this focal point was 1 cm above the surface of the liquid no breakdown of the material was seen. When the focal point was 1 cm below the surface some bubbling of the liquid was seen as the laser propagated. The spectra were collected after a 3 μs time delay (after firing the laser pulse on to the liquid) over the next 10 μs for the elemental composition, and for measuring the organics the time-delay was 1 μs which yielded information on molecular bonds.

For the analysis of the arrays of this invention, the focal length of the excitation laser, its wavelength, pulse energy, and the delay time, will have to be picked for a given liquid volume. This will minimize the issues related to splashing of the liquid and its interference with emitted spectra. Further, to reduce contamination, the sample chamber should be vented (e.g., see U.S. Pat. No. 6,741,345 which uses a blower and a collector effectively) to eliminate/reduce any deposition that may interfere with the analysis. Further, when a liquid array is used, it is preferred that the liquid level in all the elements (or the wells) be similar. This results in similar dynamics of the liquid volume/laser interaction, when focused at the surface. Since typically the plates have similar well sizes for all elements, the volume of solution in each one should be similar and within ±15% and more preferably within ±3%. Further, when the repeated pulses are used to analyze the same well several times in order to obtain better results by averaging, it is also preferred that the time duration between the pulses be such so that splashing and surface perturbation subsides from one pulse to the next, and it is also preferred that spatially the position of laser to the sample is separated. Depending on the diameter (or cross-sectional area) of the well or array element, this time will be in the neighborhood of a fraction of a Hz (e.g., 20 ms) to a few seconds (e.g., about 5 s). Shorter time periods are preferred, as that allows one to take more measurements within the same time period.

It is not necessary to only use one wavelength and/or one pulse to excite the samples. One may use a variety of combinations. U.S. Pat. No. 4,925,307, describes a method where two pulses are separated by a few microseconds (e.g., 1 to 20 μs), the energy of the first one is used to mainly vaporize the sample or to create a bubble (and hence results in weak plasma) and the second one excites the evaporated material and results in a more intense plasma. Both pulses may come from the same or different lasers. In U.S. Pat. No. 6,008,897 a UV laser (e.g. 355 nm) is used to ablate/vaporize the sample to create a plume, and another laser (IR laser at 1064 nm) is used to excite the vaporized material (or plume) so the plasma emission from the vaporized material is observed. In such cases one has to carefully time the difference between the two pulses which is typically on the order of one or a few μs. Since mostly lower wavelength pulses are generated by higher harmonics by inserting an optical multiplier in the path of the laser beam, one may use the same laser for multiple wavelengths by splitting the beam (and placing the optical multiplier in the path of one), or use two different lasers. One of the beams (i.e., pulse) from the same laser may also be retarded by putting an optical element in the beam path which retards the light velocity and/or increases its path length. Also, as a variant, the first laser beam may come down normal to the sample surface, and the second laser beam may be collinear or perpendicular (orthogonal) or at an angle to the first laser to excite this plume. Several references for this are provided in US patent application 2002/0093653. The same patent application also provides a method where two different wavelengths simultaneously impinge on the sample (or with a small separation of about 1 μs or so) that increase the quantum yield in the plasma. The shorter wavelength was found more effective in ablating the material without creating a large splash, and the longer wavelength was more effective in ionizing the material to create the plasma. In this case the preferred beams had wavelengths of 355 and 1064 nm. These can be generated by the same laser as the beam can be split in two and one of them passed through an optical element that triples the frequency. The energy of the two wavelength pulses may need optimization for highest yields, which may be selected by using an appropriate beam splitter and the source.

Optical fiber cables may be used to transmit the plasma signal to a detector, and these fiber cables may also be used to carry the laser signal which excites the sample. For the latter, one has to be careful in the choice of fibers, so that the damage threshold of the fiber is higher than the energy density that it has to carry. The same optical fiber bundle may be used to deliver the energizing laser and also to carry the signal from the plasma emission (see U.S. Pat. No. 6,762,835).

LIBS is presently used to analyze multiple solid samples on a cassette in the pharmaceutical industry. As an example Pharma Laser (Quebec, Canada) has commercialized a system called PHARMALIBS™ 250. This can analyze 100 pills when loaded on a cassette. Depending on the analysis required, this may analyze several spots on the same tablet, or the same spot several times to get a depth profile, or other combinations of desired analysis.

For liquids, microwell plates have been used for a long time in biological analysis for high throughput but these have not been used for analysis by LIBS. Some techniques were discussed earlier for analyzing flowing liquids or liquids in deep isolated containers, or in molten metals to reduce splatter which can be used here as well (e.g., lasers of different wavelengths, use of twin lasers or beams, use of proper time delays and probing frequencies, controlling laser pulse energy, pulse width, defocusing and the focal length, etc.). To get around the splattering problem of liquids, single samples of aqueous liquids have been solidified in a variety of ways. For example this has been accomplished by reacting the aqueous liquid with calcium oxide (Diaz, D. M., et al, Analysis of heavy metals in liquids using Laser Induced Breakdown Spectroscopy by liquid-to-solid matrix conversion, Spectrochimica Acta, Part B. Vol 61, p-929 (2006)) or absorbed on to porous media, e.g., wood and paper (Chen Z., et al, Analysis of heavy metals in liquids using Laser Induced Breakdown Spectroscopy by liquid-to-solid matrix conversion, Spectrochimica Acta, Part B. Vol 63, p-64 (2008); Yaroshchyk, P. et al, Quantitative analysis of wear metals in engine oil using LIBS: the use of paper substrates and comparison between single and double pulse LIBS, Spectrochimica Acta, Part B. Vol 60, p-1482 (2005)), or ion exchanged by passing the solutions with toxins in ion-exchange columns and then analyzing the ion exchange resin (Dockery, C. R., Speciation of chromium via laser-induced breakdown spectroscopy of ion exchanged polymer membranes, Applied Spectroscopy, Vol 59, p-252 (2005). However, none of these methods have been used effectively for analyzing multiple samples automatically in an array format. In part, some of these methods take a long time and large effort for sample preparation (e.g., sending each sample through an ion exchange column), some of these are only suitable for aqueous solutions within a certain pH range (e.g., reaction with calcium oxide), and for others where wood and paper was used, it was not shown that splatter can be reduced to an extent that an adjacent well cannot be contaminated, and so serious effort was made to study splatter as a function of various porous media (e.g., pore size, and the material of construction) and its relationship with the amount of liquid soaked in this. For all these reasons and also not recognizing the novelty, a multiwell plate analysis was never developed that utilizes LIBS. low viscosity aqueous liquids are difficult to analyze by LIBS as they splatter when the laser with high energy is directed at them, and if other samples are present in the vicinity they can get contaminated. However, to analyze a large number of liquid samples which are in close proximity to each other on a plate will require additional procedures/steps as described in this invention. In addition all of the above methods may be adapted if these can be shown to reduce splatter within the geometric constraints.

Figure 1:
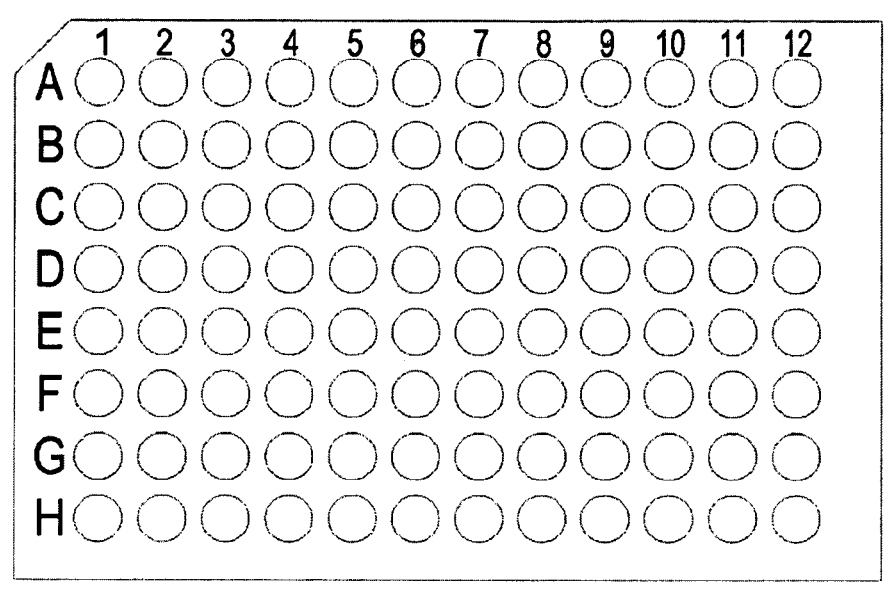

The discussion below relates to the use of multiwell plates in the biological industry which will be useful to understand the present invention. Typical plates with microwells are available in standard size with 24, 96, 384 and 1536 wells (a supplier for such products is, Fisher Scientific, Pittsburgh, Pa.) where a typical plate size is about 8×13 cm. Samples in array or microwells can provide high throughput analysis by LIBS if the test can be configured properly. Using an autosampler on an ICP instrument can take almost 6 hours to analyze 90 samples by either AES or MS (Mass Spectrometer), or even using an atomic absorption spectrometer (AAS). During this period, the calibration curves may shift and one may have to check these periodically, extending the analysis time further. As a comparison, a plate with 96 wells (or samples) in a high throughput system is read in the order of a few minutes (usually less than 30 minutes, typically less than 5 minutes). Some of the wells (typically 4 to 12) are occupied by the standards so that the standards are read at about the same time as the samples, and the unknown concentrations in the samples are detected by calibrating against the standards. The wells holding the calibration standards, blanks, blind samples, can be in a particular row or column or be distributed in any order within the plate. This is also different from conventional instruments, where the instrument has to be calibrated first in order to read the samples. In the array format all the wells are read for optical signal. The software tool then picks out the calibration wells as indicated by the user, fits a curve through these and provides the concentration for the unknown samples. Since the samples being read are not destroyed (in LIBS only a tiny fraction of the sample is ablated, thus the same well can be analyzed repeatedly), one can read the plate and then come back and read the calibration samples again to ensure there is no signal drift. In these plates some of the wells may also be reserved for internal and sample check references. FIG. 1 shows a schematic of a 96 well plate. The rows and columns are designated by a matrix of letters and numbers. For example, well B4 will be the well in the second row of the fourth column. As an example standards can be in a column from A1 to H1 or in A6 to H6, or in a row or in wells distributed throughout the plate. Some of these may be standards for calibration, while the others may be standards to check or verify the accuracy of the results, particularly if some of the results are extrapolated. It is best to use standards in the range of highest interest, and then use some of the wells with predetermined concentrations that are extrapolated and are only of cursory interest. As an example for beryllium since the regulations call for testing from 0.2 to 3 µg, one may use most standards narrowly bracketing this range to get good accuracy. However, to test the accuracy of detection capability or to test if the values are exceeding the highest numbers by a significant amount, one may use samples that are 2 to 10 times in excess or less than the highest and the lowest numbers respectively. For example one may use standards corresponding to 5, 1, 0.2, 0.05 and 0 µg for calibrating the range of high interest. The samples corresponding to 20 µg and 0.01 µg may be also included to check the extrapolation outside the range of higher interest and to check the detection limit of the method respectively. Another way to work with large dynamic ranges is to calibrate on a log-log scale. Typically this is useful when the range of interest is more than two orders of magnitude (i.e., a difference of 100 times or more). A significant advantage of the optical methods (including LIBS) is the speed at which the plates or arrays can be read. This allows a laboratory to purchase a single machine which can process thousands of samples that replaces a bank of traditional ICP machines which are highly expensive. Further, in the commercial plate readers available for biological samples one can typically read in a number of formats, i.e. at different wavelengths or different modes such as X-ray fluorescence, optical fluorescence, optical absorbance, polarized optical fluorescence, etc. LIBS may also be configured so that the samples may be analyzed in different ways (e.g. the plates may also be read for fluorescence, absorbance, polarized fluorescence) to get more data or improve the quality of the data.

In the method of this invention, one directs the optical (laser) beam at each well, and then induces a small amount of the liquid to be ablated which is then analyzed with optical spectroscopy for elemental composition. This method allows one to determine many elements simultaneously as is the case with other spectroscopy such as atomic absorption spectroscopy. The laser beam may be directed to each well using fiber optics and also the emission may be captured by a fiber optic cable that is moved in unison and the output is fed to a spectrometer. Although LIBS equipment is available from a variety of sources, a particularly preferred one uses fiber optics as described above. A supplier of this instrumentation is Ocean Optics (Dunedin, Fla.). In refinement of this technique LAMPS (Laser Assisted Microwave Plasma Spectroscopy) has been developed. The microwave is used to assist and enhance the duration of plasma discharge created by the laser beam. When a microwave is used as in the LAMPS system, one has to ensure that metals are not introduced into the cavity. For the purpose of this invention LAMPS and LIBS are not differentiated, as the former is a subset of the latter. The spectrometer has generally a range in the region of 200 to 1000 nm with a resolution of about less than 1 nm, and preferably about 0.1 nm or lower resolution. These detectors are typically CMOS (Complementary metal-oxide-semiconductor) or CCD (Charged couple device) arrays. These can collect tens to thousands of spectra per second, thus allowing one to average the data for better signal to noise ratio. Typically the plasmas generated are stable over a few ms, thus one has to use spectrometers and associated accessories to collect data in a short time interval. The laser used in the LAMPS system is a pulsed Nd:YAG. This laser has an optical output at 1064 nm. Optical elements may be used to change the frequency of the output, typically to twice, thrice or four times the value, which reduces the wavelength to half (532 nm), a third (355 nm) or to a fourth (288 nm) respectively. This allows one to select the optimum wavelength for the application. Since most of the environmental samples are extracted in an aqueous medium, twin lasers may be preferred that are fired in quick succession after one another to keep the surface perturbance low, where the first one vaporizes and creates plasma, but the second one ensures that the plasma stays long enough to be detected. The laser may be focused on the meniscus of the liquid in an area that is smaller as compared to the area of the well. The energy on the meniscus may be varied by focusing. However, a desired focusing spot area is preferably ⅕ or less than the well diameter, and also one needs to keep the damage threshold of the material in mind. The sample stage can be configured similarly to the commercial readers (described earlier for fluorescence and absorption) in terms of features where this may be heated or have a vibratory mode for shaking. X-Y (and Z) translation (or rotation) for a plate with multiple samples is done automatically either by moving the optics or moving the sample table. There may also be illumination inside the sample compartment with a vision (camera) system to ensure that the placement of the well can be verified. This illumination system (e.g., a light emitting diode) is turned-off when the measurement is carried out. One may also scan the same wells several times at different x-y locations. Plates could be made for different volumes, as an example, one may make 96 well plates with a volume of about 50 µl to 1 ml or more and 384 well plates may be made with volumes of about 10 µl or more. Since the plates have a notch on one of its corners, the sample compartment may be made to accommodate the plates only in one way. The robotics that is used with the liquid handling system to make this plate, may be used to place the plates and remove them after measurements automatically. Typically the software driver in the optical readers for fluorescence and absorption are compatible with the robotics, and the same may be done with LIBS for seamless operation.

This invention is directed to the analysis of samples by LIBS in an array format after the material of interest has been extracted into a homogenous matrix. The matrix in most cases is a liquid and that is where significant part of the disclosure is directed to. However, one may obtain uniform solid arrays made from the homogenous matrices which results in uniform array-elements. The discussion that follows immediately is directed to the extraction of materials in a uniform matrix before returning to more specific measures one can take to analyze and form these arrays. The disclosure later deals with making these arrays by automatic liquid handling systems.

Another bottleneck to high throughput analysis using conventional methods is the labor involved in sample preparation which adds both to the cost and time. Typically, samples are brought to the analytical laboratories in bulk form or as air filters or wipes which are then processed so that the analyte is extracted into a liquid medium. This preparation is usually cumbersome. This may also result in errors and fatigue leading to injury, e.g. Carpal Tunnel syndrome due to repetitive actions such as pipetting. This step can also be automated particularly for preparing arrays or microwell plates. These automation platforms are available for biological analysis and have not been advantageously tooled and used by the analytical groups, particularly the environmental and industrial hygiene industry. It is preferred that the sample prep for preparing arrays of analyte be automated to reduce labor and chances of contamination. It should be pointed out that this automation is not necessary for practicing this invention related to the analysis of arrays by LIBS. Optionally, one may only automate a part of the liquid handling system, where plates are prepared from liquids obtained by pre-processing of samples. This part of automation ensures consistent volume that is dispensed on to the plates.

Some of the standard methods of use in the industry to analyze select toxic materials for the environmental and industrial hygiene applications are given in Table 2. Most of these methods use ICP-AES or ICP-MS for analysis. Table 3 gives the values of these materials that are allowed by the various agencies. Clearly any analytical method (including the one being discussed here) should provide a limit of detection which is at least a factor of two and preferably a factor of 10 lower than these values.

In all of the methods listed in Table 1, part of the test protocol is to obtain the material of interest from the media (surface wipe, air filter or soil) into a liquid, and then subject that liquid to analysis. The issue with conventional AES and MS which is used for most of these tests is that they take too long and require too much of sample for analysis. Some of the other methods listed in this table such as optical fluorescence and absorption are fast and can be analyzed in an array format, but they are highly specific to a single element due to the unique chemistry required of the binding dye. However, using LIBS provide the same advantage to analyze liquids for multiple elements in an array format and at rapid speeds.

TABLE 2

| Material to be analyzed | Standard methods using ICP-AES and ICP-MS, AA | Standard Methods using optical and X-ray fluorescence |
|---|---|---|
| Arsenic | OSHA ID105 EPA SW846-6010, 6020, 7061, 7062, 7063 | |
| Beryllium | NIOSH 7300, 7102, 7301, 7303, 9102 OSHA ID125g, ID206 EPA SW846-6010, 6020 | NIOSH 7704, 9110 ASTM D7202 |
| Cadmium | NIOSH 7300, 7048, OSHA ID121, ID125g, ID206, ID 289 EPA SW846-6010, 6020 | |
| Chromium (Hexavalent) | NIOSH 7605, 7604, 7600, 9101 OSHA ID215, W4001 EPA SW846-7195, 7197, 7198, 7199 | NIOSH 7703 EPA SW846-7196 |
| Lead | NIOSH methods 7082, 7103, 7300, 7505, 7701, 9100 and 9105 OSHA ID121, ID 125g, ID206 EPA SW846-6010, 6020 | NIOSH Methods 7700, 7702xrf |
| Mercury | NIOSH 6009, OSHA ID140, ID145 EPA SW846-6010 EPA SW846-6010 | |

TABLE 3

| Material | OSHA | NIOSH | ACGIH | EPA | DOE |
|---|---|---|---|---|---|
| Arsenic | | | Air 10 µg/m$^3$ | Water 10 µg/l | |
| Beryllium (air) | 2 µg/m$^3$ 5 µg/m$^3$ | 25 µg/m$^3$ (Peak) | 0.5 µg/m$^3$ | 2 µg/m$^3$ | 0.2 µg/m$^3$ (action limit) |

TABLE 3-continued

| Material | OSHA | NIOSH | ACGIH | EPA | DOE |
|---|---|---|---|---|---|
| Beryllium | (Ceiling) | | | Water 0.004 mg/l | Surface 3 μg/100 cm² 0.2 μg/100 cm² (Release level) |
| Cadmium | Air 5 μg/m³ | | Air 10 μg/m³ (total) 2 μg/m³ (respirable) | Water 0.005 mg/l | |
| Chromium (Hexavalent) | Air 100 μg/m³ | Air 100 μg/m³ | Air 100 μg/m³ | | |
| Mercury (inorganic) | Air 100 μg/m³ | Air 50 μg/m³ | Air 50 μg/m³ | Water 0.002 mg/l | |
| Lead | Air 50 μg/m³ | Air 50 μg/m³ | Air 50 μg/m³ | Water 0.015 mg/l | |

ACGIH: American conference of Government Industrial Hygienists'
DOE: US Department of Energy As an example, for beryllium, the federal regulations for the Department of Energy (10CFR850) state that airborne contamination in the work space must be less than 0.2 μg/m³, which is generally measured by personal samplers (carried by workers in beryllium contaminated area) over an eight hour shift. This is a time weighted average (TWA), where the air is sampled over an eight hour shift and the filter from the sample is then analyzed. Similar standards are established for the other toxins in the work place, particularly for lead, mercury, cadmium and others as listed in Table 2.

As a first step for most methods, the contaminant is drawn from a heterogeneous solid matrix in a liquid solution (unless the contaminant is already in liquid, such as water and oil). This is done either by dissolution (or extraction of the contaminant or components including the contaminant) or by dissolving of the solid. One may use solutions from known methods to totally digest the sample in order to get the analyte in the solution. For example, for beryllium, the methods from Environmental Protection Agency (EPA) such as SW846-3051 and 3050, or OSHA125G or NIOSH 7300 use concentrated acid, such as nitric acid, which may be mixed with hydrogen peroxide and concentrated hydrochloric acid, or one may use ammonium bifluoride aqueous solution, as given in NIOSH procedures 7704 and 9110 or ASTM D7202. The following methods use atomic absorption spectroscopy and hence qualify as methods that could be adopted for analysis with LIBS. This list is not exhaustive. Some of the standard methods using atomic emission spectroscopy are ASTM D4185; NIOSH 7300, 7104, 7301, 7303, 9102; and OSHA ID-121, ID-125G, ID-206.

One may analyze the materials by LIBS using high throughput methods after extracting them in a homogenous liquid mixture in several ways. Some of these are
  a. Analyzing arrays of solid stains after drying the homogenous liquid samples.
  b. Analyzing homogenous liquids array in multiwell plates
  c. Analyzing arrays of porous media soaked with homogenous liquids (including those where the viscosity of the liquids is modified or they are solidified by a gelation process or combination of these)

The arrays may also include internal references, calibration standards, blanks, and check points along with the samples to be analyzed. Each array plate in the sample compartment will have at least two samples, but preferably more than 12 and most preferably more than or equal to 24. In LIBS where a tiny part of the sample is ablated, it is best to construct the sample compartment interior with corrosion resistant materials as even a small amount of vapor generated from the acids may lead to corrosion over a longer time period. Many of the corrosion resistant materials and processes for putting down their coatings are described in the liquid handling system section.

For the first array type, one can form stains by drying the homogenous fluid. The important issue is that these stains should be homogenous in composition to the point so that its average amount is represented within the ablation area/volume, and preferably these stains are uniform in thickness. In order that drying does not cause phase separation it is best if the plate is made out of a porous membrane located on top of an impervious plate. Those porous membranes are preferred where there is no cross-talk between the pores and the pores are sealed by the impervious plate at the bottom. An example of such porous membranes (or filters) plates are Isopore® membrane filters from Milipore (Billerica, Mass.), track etched membranes from GE (Schenectady, N.Y.), Anopore membranes from Whatman Plc (Whatman is now a part of GE Health Care Life Sciences Ltd of United Kingdom). This will allow the liquid to dry in each pore separately of the adjacent pore. Further, the orientation of the pores should preferably be only in vertical direction and not connected in X-Y direction. The cross-section (size) of the pores should be preferably about 1/10 the size or lower as compared to the spot from where the material is ablated. Typically the laser beam is focused on a spot size that ranges from about 20 to 1,200 μm in diameter. After the filters are dried, the plate is carried over to the instrument and analyzed. One has to make sure that drying in the filter is uniform not only through the filter thickness (unless the filter is completely ablated through the thickness) but also the fluid sticking to the plate.

Figure 2B:
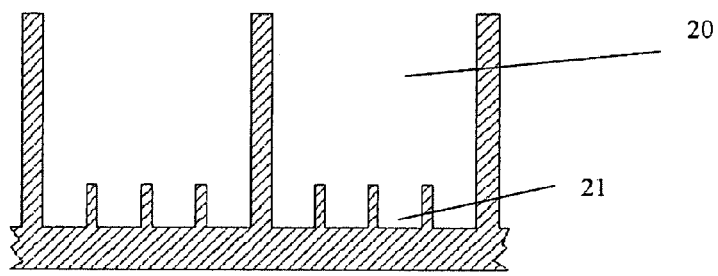
FIG. 2b: Front view of textured microwell plate.

One may have a plate with a shallow texture as described below to create uniform solid stains. FIG. 2a shows a plate with an array of twenty four array-elements (20). Only two elements on the left top corner show the texture of these array-elements which are divided in smaller patterns called microfeatures (21). The figure also shows a laser beam (200), that is interrogating the first array element. The size of the array element may be much bigger than the size of the laser beam so as to allow the laser beam to interrogate at several different spots within that array element if desired. FIG. 2b shows details of the first two array-elements taken along the section A-A in FIG. 2a. The size and widths of the walls are only schematic. FIG. 2b shows the array-elements (20) and the microfeatures (21). It is preferred that the height of the array element walls 20 and their width be greater as compared to that of the microfeatures. This helps in keeping the liquid from spilling from one array element to the next and in also identifying the different array-elements distinctly. When the homogenous fluid is put in these array-elements for drying, its volume should be such so that it just comes up to the height of the microfeature walls so that all microfeatures are filled equally. As the drying takes place the liquid levels recede and each microfeature dries independently of the next one. If instead of texture, porous media with vertical pores are used (as discussed above), the liquid level to form homogenous drying should be just to or above the thickness of these filters (which are put in wells deeper than their thickness). Even if there is inhomogeneity in drying within one microfeature it is not that important, as the laser spot is much bigger than one microfeature and encompasses several of them. Thus the sampling of material by the laser results in the analyte of interest being represented homogenously. Where samples are analyzed in liquid state, the microfeatures within each array element should preferably communicate with each other (e.g., at the bottom) so that the liquid level in all the microfeatures is constant. One may also create microfeatures by creating lines of hydrophobic areas (for aqueous solutions) instead of physical walls so that the liquid will recede from these areas and form drops in each of the hydrophilic areas within these and dry independently. To reduce peeling of the dried material and to ensure that all of the depth can be ablated (to overcome any issues related to heterogeneities through the thickness) it is preferred that the thickness of the dry material be less than 5 microns and preferably less than 2 microns. Peeling may also be reduced by treating the bottom of the plate (or well) with a non-interfering adhesion promoter. One may also smear a thin liquid film on a surface and then analyze this. The liquid is thin enough (usually a few microns in thickness or less) so that the surface tension/viscosity will provide enough of a drag on the boundary layer (between the liquid and the substrate) to prevent the ejection of the liquid due to the shock way. One may also form an array element comprising of several smaller islands (preferably smaller than the focus spot of the laser beam) of liquid film so that the shockwave is not easily transmitted through the liquid from one island to the other. As an example, for aqueous solutions one can form islands of hydrophilic areas on the substrate surrounded by hydrophobic perimeter, and each array element can comprise of several of these e.g., see U.S. Pat. No. 7,195,872, PCT application (WO/2004/029586) and Zhang, H. et al. (Recyclable Hydrophilic-Hydrophobic Micropatterns on Glass for Microarray Applications. *Langmuir*, 2007, 23 (9), pp 4728-4731)

For the liquid arrays, with finite depth in the thickness direction, where each array element is divided into smaller cells, the microfeatures (or cells) with closed pack shapes are preferred, e.g., rectangles, squares, triangles, hexagons, mixtures of hexagons and pentagons, and irregular geometries (e.g. see Anopore® membranes as described below) to name a few. The individual array element need not be closed packed, and one preferred shape is circular. To physically distinguish one array element from the other, one can use inter-element walls that are colored, or with different optical characteristics, or walls that are wider or higher to easily distinguish between them. These may also be formed at the bottom of the well plates so that during staining there is no possibility of cross contamination. The bottom of each well plate may comprise of features to accommodate one or several spots. Since these areas will be subjected to excitation laser which may ablate part of the substrate as well, it is preferred that the materials of construction of the substrate should not interfere with the analysis and preferably not comprise any of the elements that need to be analyzed. These should have low absorption for the laser beam, and one may tailor the wavelength as described earlier to achieve low absorption for the substrate but high yield for the sample. Preferred ways of forming these textures are by molding, embossing and etching. The processes and the type of microfeatures that can be formed are described in detail in U.S. Pat. No. 7,195,872 the entire disclosure of which is included herein by reference. There may be instances where LIBS may be used for biological analysis. As an example, one way of doing the label free detection of biological materials and drugs is by looking at the elemental composition. For example usually different drugs have unique elements such as chlorine, bromine, fluorine, sodium, potassium, selenium and a variety of other elements (e.g. see US patent application 2005/0214847). When biological samples (tissues, blood, nucleic acid, an oligonucleotide, a peptide, a polypeptide, a protein, an enzyme, a cell, an organelle, a lipid, a carbohydrate, a fat, a vitamin, a nutrient, or an antibody) are exposed to drugs they may selectively bind to some of these. One can analyze these materials and if the element of interest is present, that will demonstrate the binding of the drug. As mentioned earlier LIBS may also be used to provide information on the presence of specific molecular bonds in order to facilitate direct observation of specific molecules (organic or inorganic)

Figure 3:
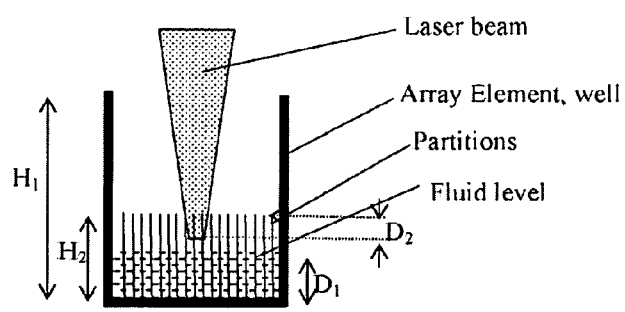
FIG. 3: Schematics showing the relationship of the partitions in a array element and its relationship to the focus of the laser beam and the liquid level.

For liquids where microwell plates are used one has to be careful about the splatter of liquid from one well (array element) to the next to avoid cross contamination. The splatter takes place by ablating part of the liquid with a high energy laser beam which causes a shockwave through the liquid. One way to reduce the spatter is to divide the volume of liquid in many smaller cells so that the shockwave is not easily transmitted from one cell to the next. The energy of the shock wave is dissipated by perturbing the liquid in these small pores where due to friction and drag such energy is expended. For this, the type of arrays mentioned earlier for producing solid arrays, may also be used here with liquids (i.e. without drying). Some of the inserts that can be put inside the wells to divide the well in small microvolumes (or cells) that may have pore size ranging from nanometers to several microns. The pores may be isolated or interconnected. It is highly preferred that the pore size (or the average diameter or restriction of the porous media) be smaller than the size of the focused laser beam. The surface tension interaction between the fluid and the insert may be low or high, and some may be more suitable in an acidic or basic media. Some of this media for the insert are various types of sponges or filters, These filters may even be stacked on top of each other to get a desired total thickness. Some examples that are available from Fisher Scientific (Pittsburgh, Pa.) are GE and Isopore® polycarbonate track etched membranes (pore diameter from 0.05 to 8 μm), Whatman hardened ashless paper (pore diameter from 0.25 to 25 μm), glass and quartz fiber membranes with and without binder (pore diameter from 0.2 to 6 μm), Teflon (pore diameter from 0.2 to 5 μm), etched nylon (pore diameter from 0.2 to 20 μm) and Anopore®, aluminum oxide (pore diameter from 0.02 to 0.2 μm). Other typical materials are polypropylene, cellulose ester, polyvinylidene fluoride, and polytetrafluorethylene. Further, these can be hydrophilic or hydrophobic. FIG. 3 shows an array element or the well with small partitions (or the porous media). Also shown is the fluid and the incoming laser beam (detector to read the emission is not shown). The distance between the focal point and the porous medium is shown as $D_2$. This number could be positive or negative (i.e., the focus point is below the top surface of the partitions as shown, that means that this value is negative). The height of the porous medium (H2) in relationship to the well depth, liquid depth (D1) and the focal point in relationship to the height of the porous medium can all be adjusted, so that splatter is eliminated and a high signal of the elements in the liquid is obtained. These adjustments will be determined by the morphology, mechanical and optical properties of the material of the partitions and the liquid characteristics. FIG. 3 is only a schematics, in practical terms due to the capillary effects the fluid level will not be as clearly defined, but one can control its volume relative to the porous medium (or partitioning medium) and the surface tension between the liquid and the porous medium. When the samples are solidified by the use of gelation/viscosity additives as described below, then the height of the partitions and the fluid level is the same.

To improve the meniscus, surfactants may also be added to the solutions being analyzed. Since the surfactants mainly concentrate on the surfaces, one has to be careful to ensure that the analytical results are not compromised as disproportionately larger amount of the surfactant may be ablated. These surfactants may be ionic (cationic or anionic) or nonionic. These are preferably present in quantities of less than 0.1% of the solution volume, and preferably less than 0.01% so as to keep their interactions low. Some examples of such surfactants are Triton® X100, Triton® X-114, Triton® X-405, Novec™ FC4430, Novec™ FC4432, Novec™ FC4434. The first three are available from Aldrich Chemical Co (Milwaukee, Wis.) and the last three from 3M (Minneapolis, Minn.).

Other ways to avoid the splattering comprise of the increasing viscosity of the fluid matrix or change its physical state so that other ways to dissipate the energy in the shock wave can be initiated. To change the viscosity, one may add thickener (e.g., inorganic material or organic polymer) to each of the wells, Those viscosity modifiers are preferred that result in thixotropic properties, so that they are able to offer a very high resistance to instantaneous viscous deformation, but are able to recover their homogeneity and meniscus with time. These materials may also form physical or chemical crosslinks. Since in most cases the solution will be aqueous based, some of the materials for this purpose are hydrophilic fumed silica (available from Cabot (Billerica, Mass.) as H5, M5, ECT5 and from Evonik Industries (Orange, Calif.) as Aerosil® 200, Aerosil® 300 and Aerosil® 380), fumed aluminum oxide Aeroxide® AluC and fumed titania as Aeroxide® TiO2P25 from Evonik. Hydrophobic fumed silicas and other such products may be used for oil based samples. Polymeric materials that result in mechanical (including flow) properties of aqueous fluids are crosslinked or non-crosslinked polyacrylamide or polyvinyl alcohol. Typical polymeric/viscosity modifier content is less than 10% by volume. One may also use ionic polymers such as polystyrene sulfonic acid:sodium salt (PSSNa) that may be crosslinked or non crosslinked. These ionic polymers may be acidic (PSSNa) or basic (polymeric chains with ammonium pendant groups), and they may also be crosslinked as in ion exchange resins. Use of crosslinked polymers will solidify the liquid by formation of a gel. A number of such products are available for cosmetic and food industries, e.g., corn starch, and the product Stabilize QM from International Specialty Products (Wayne, N.J.) swells when it interacts with water. Some of these materials may provide the right characteristics in a limited pH range, and one has to assure that their use does not cause inhomogenieties to occur due to phase separation and that these will not interact with the analysis at hand. Similarly for oil based fluids (e.g. machine oils) appropriate polymers compatible with the fluid may be used. These materials may be added to the wells before pouring in the analytical fluids or later or may even be part of the wells (e.g. a coating) which swell upon the addition of liquids. One may even conduct polymerization or crosslinking after the fluids are added to the wells. Another way to take advantage of the small volume of liquid in the wells, is to freeze the test solution by lowering the temperature of the plate. In all cases, one has to ensure that during the process we do not create heterogeneity by phase changes so that the volume ablated by the laser is representative of the original sample. Solidified homogeneous media can dissipate the shock wave by viscous, elastic or viscoelastic deformation. One may also combine solidification and the physical microfeatures.

In all cases one may use a blanket (preferably flowing) gas so that the properties of the plasma are consistent. Some of these are oxygen, nitrogen, argon and helium.

Figure 4:
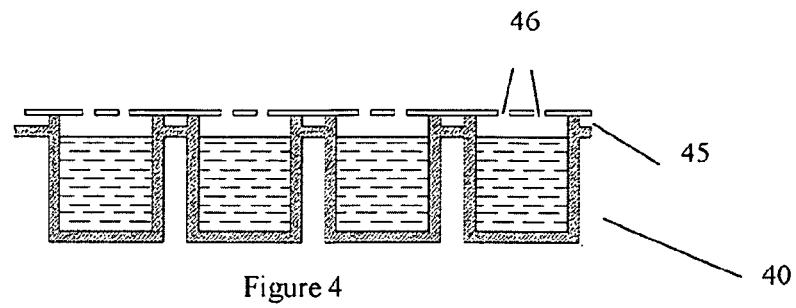
FIG. 4: Microwell plate with cover.

Another way to address this issue is by using a sealing lid on the microwell plate. This sealing lid is permeable or transmitting to the laser beam and to the emission spectra and/or to the ablation products resulting from the interaction of the laser beam and the fluid in the well but not to the liquid splatter. One way is to ensure that the lid is transparent to the laser wavelength or there are perforations in the lid for the laser beam to be transmitted to the sample. As shown in FIG. 4, one way to achieve this is to have a hole (46) in the sealing lid (45) with a typical hole size of 0.1 to about 2 mm. It is preferred if this hole be greater than about 10 times the laser beam size at the point where it enters the hole. The small size of the hole contains the splatter (as it reduces the probability of the fluid to be ejected from a small hole and enter an adjacent cell also through a small hole) while allowing the laser beam to go through and the ablation products to come out. One way to sample many areas in the same well (or array element) through one hole is by moving the incoming laser. The angle of the laser beam in reference to the sample surface can be kept the same or varied. One may have more holes as shown in the figure, where one hole is for the laser and the other(s) for the ablation products. The holes may be circular or any other shape (e.g., oblong) for laser or a fiber optic probe to enter the well at an angle. One may even have a laser go through the lid as long as it is transparent to the laser, and the ablation product come out through the hole. One may have no visible holes, but the cover be made of a porous material (e.g., a foam) through which the ablation products could come out. Another way of forming the lid may be using a material with two parallel but separate planes separated by a distance, where the holes in the lower plane are slightly offset from the holes in the top plane to reduce the splatter even more but allow the entry of the laser at a desired angle. The cover may have a solid window of a material which is transparent to the laser. The cover may also have several holes (or a tight mesh) for the ablation products to come out while at the same time control the splatter. In any case there are several methods to provide for the permeability of the laser and the ablation products while keeping a lid on the microwell plate. The holes may also be used to introduce inert gases such as helium and argon to obtain cleaner spectra. These gases may be used for any of the arrays described and may form a blanket over the array plates or inside the sample chamber or within each well.

Figure 5:
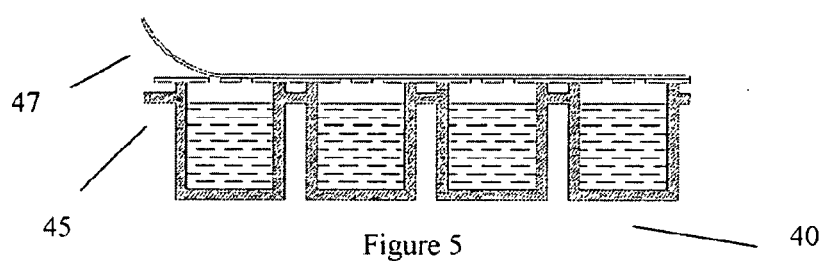
FIG. 5: Microwell plate with a removable cover.

One of the reasons to make the laser permeable window (or hole) to be about 10 times or more than the laser size going through this window is to also ensure that this alignment is not too critical. Since in a plate there would be a number of wells, one can easily align these holes based on a vision system, or a fiduciary mark on the lid or the plate to which all the holes are indexed to. Further, the lid should have some flexibility or elasticity so that it is able to slightly deform due to the sudden pressure built up in the microwell once the laser strikes, and then vent the ablation product through the hole(s) or porosity in the lid. It is preferred that the meniscus level of the liquid in the wells be within a few mm of the lid and the thickness of the lid be about 1 mm or less so that the path of travel for the ablated products is small. However, since the emission spectra is observed a few μs after the sample excitation, and it may take longer to transport ablated material from inside the well to the outside, one may use a dual laser system, where the second laser is used to excite the vapor material outside the well as described later in FIG. 8. Here the two laser beams are shown as orthogonal to each other; however these laser beams may be at any angle to each other or even collinear. The microwave cavity for a LAMPS system may be located just outside of the lid area. The lids are typically made of metal foils (e.g., aluminum), plastic materials such as polyolefins and polyester, or their laminates and are sealed by a pressure sensitive adhesive or a heat sealing adhesive to the lip on the wells as shown in FIG. 4. Non-conductive seals are preferred when these samples are to be put in microwave or magnetic cavities. There are several suppliers of sealable lids, for example, E&K Scientific (Santa Clara, Calif.), Excel Scientific (Wrightwood, Calif.) and Adhesives Research Inc (Glen Rock, Pa.). The holes in the lid may be formed by laser machining so that these are precise. These lids may be automatically applied by a module in the liquid handling system as soon as the plates are filled. It is preferred that these lids be made as one sheet to cover all the wells on a plate. After the plate is sealed it may be optionally placed in the analyzer using a robotic arm on the fluid handler. There may be another variant of the lid as shown in FIG. 5. In this case, the lid is a composite of two layers where one layer is as described above and the second layer covers the first lid and is preferably adhered to it using a release coating. This way, one does not have to analyze the plate immediately and may be stored for a while. Just before analysis, the upper layer is removed to reveal the holes or porosity in the underlying layer, and the plate is then inserted into the LIBS reader.

A third method may be where a porous material (such as ash-less Whatman filter type 541) is placed in each well. The samples are analyzed while the filters are still wet. The filter pores will contain the splatter. One may still want to use the lid as described above to ensure that the filters do not start drying too fast and cause non-uniformities. The amount of liquid should be such so that there is no visible free liquid meniscus on top of the filter but should still be wet. The pore size of filter papers being discussed in this invention can be any but a preferred range is about 0.01 to 5 μm. An extension of this idea is where a filter or a wipe or soil sample is placed in the wells of a plate. A liquid is added to wet the filter/wipe/soil. This liquid is a dissolution solution (an acid, ABF, etc for the analyte(s) of interest) which is added in an appropriate amount. A lid is placed on the plate covering the wells and the plate is then heated or subjected to microwaves. The analyte of interest is dissoluted to an extent that the well or the media in the well becomes homogenous in terms of the distribution of the analyte. These plates can then be analyzed in either wet or dry state.

Figure 6:
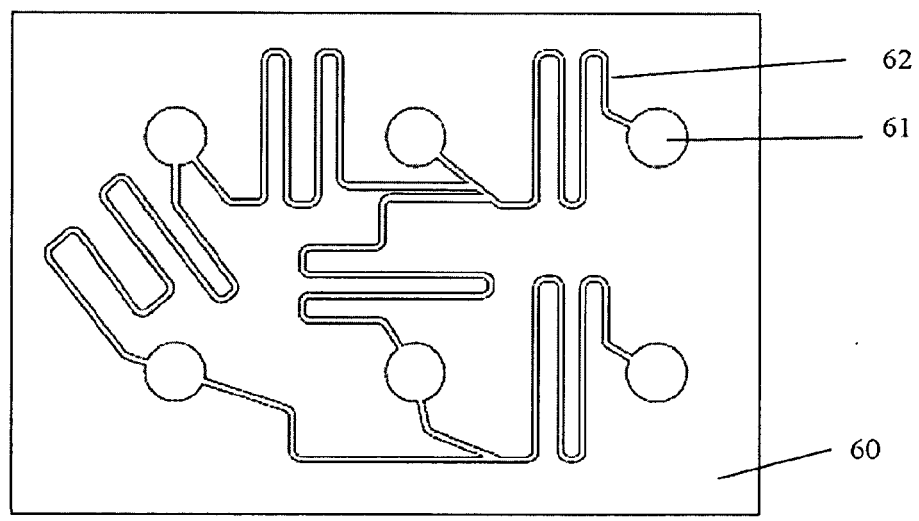
FIG. 6: An array of elements for a Lab-On-a-Chip.

The arrays are to also include Lab-on-a-chip systems which have more than one area that needs to be characterized by LIBS. As an example, such chips are available from Agilent Inc (Santa Clara, Calif.). As shown in FIG. 6, these chips (60) have multiple sample and fluid compartments such as 61 that are connected via channels such as 62. These chips enable sample handling, mixing, dilution, electrophoresis and chromatographic separation, staining and detection, etc. on single integrated systems, and the sample compartments can be analyzed for their compositions.

Figure 7:
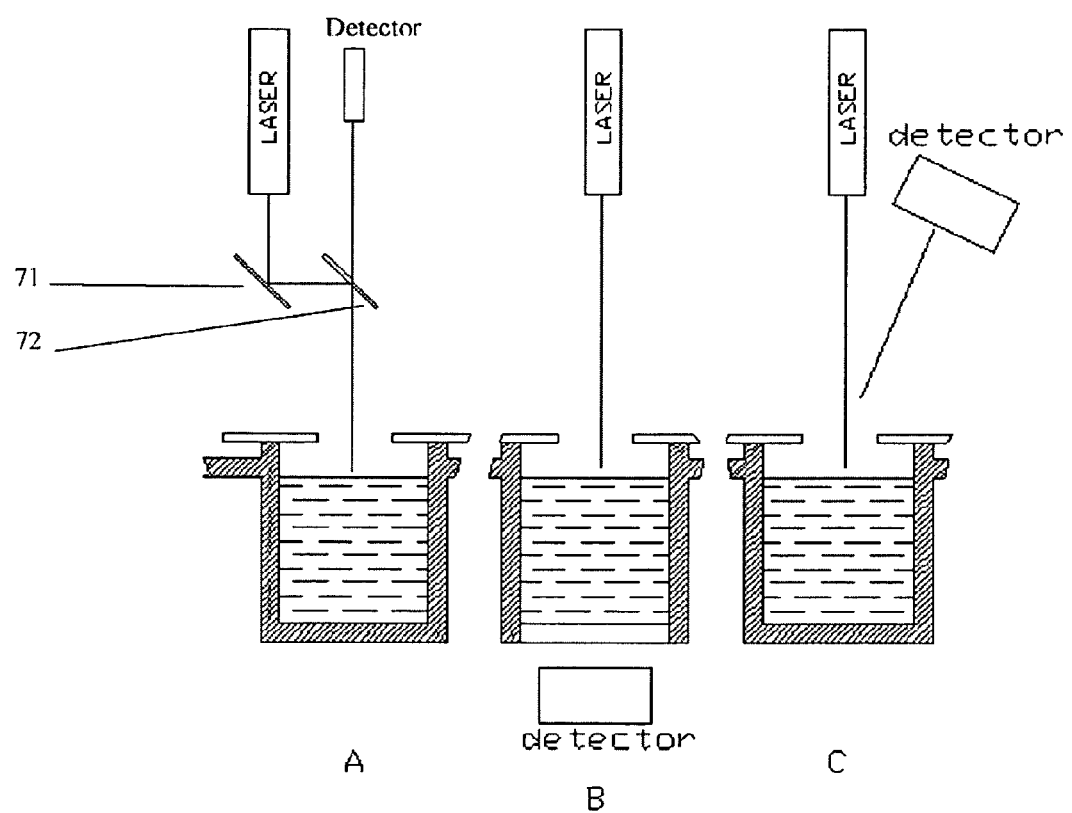
FIG. 7: Schematics of several geometric configurations of excitation laser, sample and the detector.

To contain the splatter, other methods my also be used. For example FIG. 7a, shows a hole in the lid (the dimensions of the hole are small as discussed earlier) through which both the excitation laser beam and the emission spectrum is collected. The figure shows two mirrors 71 and 72 which direct the excitation laser. The mirror 72 may have dichroic properties so that it reflects the excitation laser wavelength but lets the other emission wavelengths to pass through (or one may use neutral half mirrors with blocking filters). The hole in the lid may also be replaced by a transparent window, and this window size may cover through the entire well cross-section (or opening) at the top. The window may be transparent for the emission spectra, but may have a hole for the excitation laser. Depending on the focal length of the lenses used to focus the excitation laser this may not damage the lid, but will have sufficient energy to ablate the liquid from the surface. In FIG. 7b, the detector is located below the well. The excitation laser from the top passes through a hole or a window, and the emission spectra is recorded from below. The detector may also comprise of an edge or a band filter that will block the excitation wavelengths from entering (not shown). As an example, Corning (Lowell, Mass.) sells multiwell plates (with 96 wells) that are made out of transparent plastics (Costar® 3635). BrandTech (Essex, Conn.) also sells plates with 384 wells that have transparent bottoms extending in the UV range (product 781462). The bottom of these plates are made out of a polymer that transmits starting from about 220 nm and used for looking at the spectra to 1,000 nm. The sides of these plates are made out of polystyrene. The same material may be used for the lid for the setup in FIGS. 7a and 7c if a transparent window is needed. In FIG. 7c, the emission through the window at the top is detected at an angle.

Figure 8:
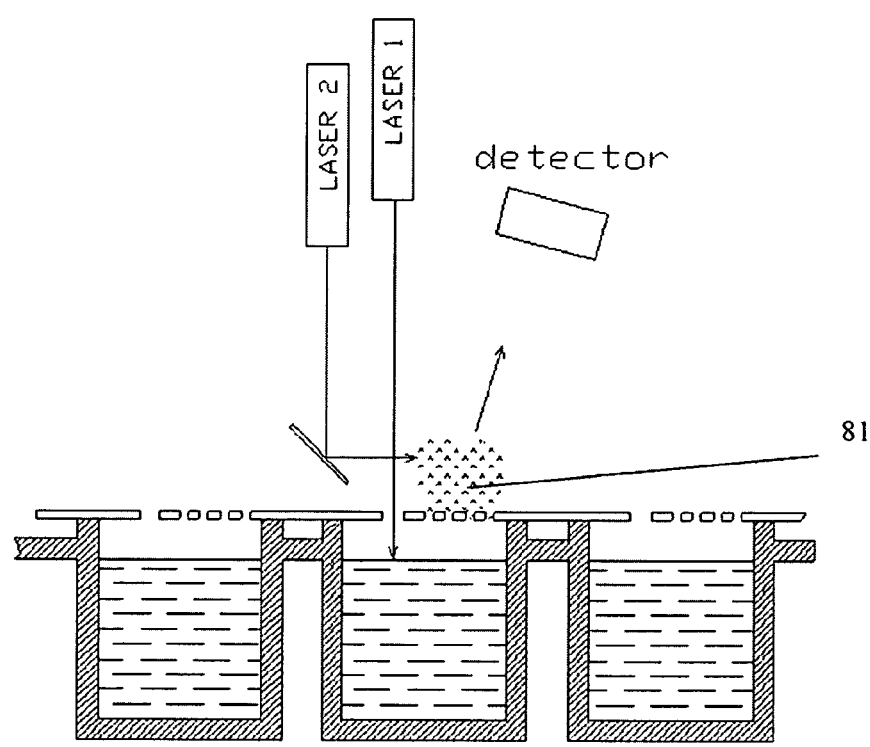
FIG. 8: Schematics of analysis of a sample which is to be analyzed by ablation and excitation in two steps.

FIG. 8 shows another way where permeability is established while containing the splatter. Laser 1 is used to ablate or vaporize the material that comes out of the lid which is porous or has holes. This material is then excited to form the plasma (81) by laser 2 (or laser beam 2). This plasma is then detected. Laser 1 and 2 may have different wavelengths, energies, pulse widths and time interval according to the principles discussed earlier. The timing between the pulses from the two may have to be carefully controlled to get the maximum plasma outlet.

Although not shown in any of these figures, a blower system may be attached to ensure there is no accumulation of the material. In the LAMPS system from Ocean optics, the microwave cavity may be located in order to enclose the plume (81) shown in FIG. 8 and may or may not require the second beam or the second beam may be collinear. There are several materials that may be used to make lids and bottoms of these array plates that are transparent in a wide range. It is easy to find plastics that are transparent from about 400 to 1100 nm, but it is difficult to find materials that are also transparent in UV. Some of the disposable plastic plates that are transparent in UV as well are described above from Corning and BrandTech. Some of the UV transparent plastics and films are Tefzel® from Dupont High Performance Materials (Circleville, Ohio) which is a fluorinated polyolefin. Another fluorinated material from Asahi Glass Company (Japan) is called Cytop®, Polymethyl pentene, polyarylate and certain acrylics, silicones (e.g., dimethylsiloxane). All of these may be employed in making of lids and bottoms that need to be transparent between about 200 to 1100 nm to accommodate either/and excitation YAG:Nd lasers or emission spectrums.

To get most out of this invention, it is preferred that an automated liquid handling system be used to extract the analyte uniformly into a matrix and the preparation of the array plate. Automated liquid handling systems increase speed, provide consistency in sample preparation and lower cost by reducing the labor. In addition for analysis of radioactive materials such as uranium and thorium it can also provide sample preparation without human intervention to increase the safety. These automated systems can also handle processing of solids (e.g., weighing and dispensing). Optical analysis methods such as fluorescence, luminescence and absorption (or change in transmission) have been developed for high throughput analysis of biological samples. The fluorescent method for beryllium and its adaptation to the microwell plates is well described in U.S. Pat. No. 7,129,093 and published US patent application 2005/0280816, published PCT application 2008/130737 and U.S. patent application Ser. No. 12/338,724 (filed on Dec. 18, 2008). All of these are incorporated herein by reference. Electron or x-ray induced fluorescence may also be used in an array format. The sample arrays are typically made by putting probes on surfaces that are separated from each other or liquid samples in plates with microwells. Examples of microarrays can be found in U.S. Pat. Nos. 5,700,637; 5,744,305; and 7,195,872 and US patent application 2003/0027129. Many of the concepts related to the liquid handling systems for preparation of the arrays were disclosed in a US patent application entitled High Throughput Methods for Analysis of Contamination in Environmental Samples (U.S. patent application Ser. No. 12/338,724).

One of several reasons for not automating the sample preparation for typical analytical chemistry methods is the high volumes of liquids that are used for sample preparation even if smaller samples are used in the final analysis. This arises as the sample in the form of a wipe or a filter or bulk soil needs larger volumes of these liquids to extract the analyte into the liquid medium. Typically in high throughput used in the biological industry, most ingredients are pipetted in 1 ml or lower quantities. In analytical chemistry one requires higher volumes and it is usual to use 5 ml to 100 ml liquids per sample. Another related reason for the lack of automation in the analytical chemistry field is the type of liquids used. In biological assays the liquids used are mildly acidic or basic (e.g., from about 4 to 9), whereas in analytical chemistry of environmental samples one typically uses strong acids and strong bases with pH usually lower than 4 or pH higher than 9. This becomes difficult to handle in large volumes with system pumps that are generally provided, as these use metals and glass components which can corrode. Use of small volume disposable pipettes (e.g., made out of polypropylene) is fine with the extreme pH range, but require several operations to dispense large volumes and reduce the throughput of the instrument in terms of samples prepared in a given time. The reason for using smaller pipette tips is related to accommodating the spacing between the separations of wells in the standard multiwall plates.

Some of the instruments for automated sample preparation are available from Hamilton Inc (Reno, Nev.) as Microstar, model 4200, 4000); from Perkin Elmer (Waltham, Mass.) as Janus; from Tecan Systems Inc (San Jose, Calif.) as Freedom EVO, Genesis; Velocity 11 (Menlo Park, Calif.) as Bravo, Vprep; from Beckman (Fullerton, Calif.) as Biomek; and from Gilson (Middleton, Wis.) GX and Quad series. For high throughput it is preferred to pump the large volume fluids through the system, so that these can be added to the processing tubes quickly and in one operation. However, when this is done, these fluids can interact strongly with the materials of construction used. As an example to pump these fluids accurately, glass syringes and metal probes (usually stainless steel) are routinely used. However, in analytical chemistry the use of such materials with strong bases or acids could present problems as most strong acids will attack and corrode stainless steel, and hydrofluoric acid used in many digestions will etch glass. In some cases if the elemental toxin being analyzed is present in small concentration in these probes or syringes (e.g., beryllium in steel and lead in glass), then the results at finer limits may be compromised. Thus it is preferred to replace these with polymeric materials or coat them with polymers to reduce their interaction with the fluids, or use those systems that do not use syringes such as Gilson's GX 281 and GX 271. Preferably the syringes and probes (fine tubes for aspirating in liquids and dispensing them from one place to the other) should be made or coated with organic polymers. Some of the preferred polymers are parylenes, polyolefins (e.g., polypropylene), halogenated polymers (e.g., polytetrafluoroethylene and fluorinated ethylene/propylene and polyvinylidene fluoride and polyvinylidene chloride, polyvinyl chloride and polychrorotrifluoroethylene), polycarbonate, polysulphone, polyacetal and polyesters (e.g., polyethylene terephthalate and polyethylene naphthalate), and also thermoset polymers such as epoxies and alkyd resins. These materials may be used for coating metallic or glass/ceramic parts. If coated, these coatings should be placed both on the exterior and the interior surfaces of the probe, while for syringes only the interior surfaces are sufficient. In most preferred cases the probes and the syringes are constructed out of the polymeric materials, with exemplary materials listed above. The procedures to make these arrays are well discussed in filed US patent application (U.S. Ser. No. 12/338,724) which is incorporated by reference herein.

Another important aspect of analyzing the well plates is the sensitivity of background to the particulate contaminants that may float on top of the wells giving rise to disturbance in meniscus or dirt that may result in signals that are distorted or not true representations of the samples. The automated processing of samples minimizes handling and reduces contamination probability. It is good practice to keep the plates covered when not in use, and handle them with gloves so that oils and dirt are not transported on to the plates which may interfere with either the transmission of the excitation laser or with the emission spectra. In addition, once the plate is inserted into the chamber, it may be vibrated or shaken for about 1 s or less in order to wet the dirt and allow it to sink or minimize disturbances on the surface.

Figure 9:
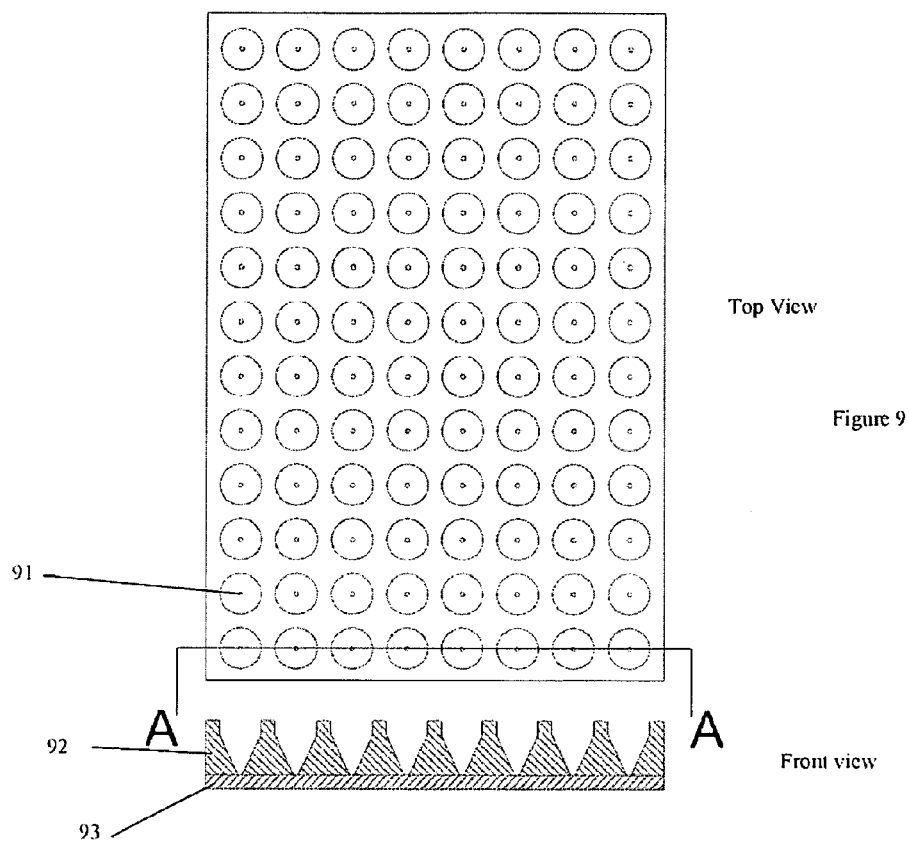
FIG. 9: A multiwell plate used for concentrating liquids or forming solid arrays on a plate.

An important area of application of such arrays is biological field where interaction of various materials is tested routinely, for example interaction of a virus with a cell, drug with a protein, etc. An important area in drug discovery is to be able to measure binding of drug molecules to proteins without the use of any labels on the drug or the proteins. The radio or fluorescent tags can interfere with such binding leading to false conclusions and interpretations. As an example one may send a biological target through a size exclusion column so that it is trapped. Next a drug molecule without label is sent through the same column. If the drug does not bind to the biological target, its size is such that it is not trapped by the above column. If one wanted to study a variety of biological targets each in a different column or a variety of drug molecules or chemicals, one can have various columns. These columns (or parts of it) may be arranged in arrays and analyzed by LIBS, and it will not be necessary to dry them as these will be already contained in porous media. If the drug molecule has elements not present in the biological molecule and the column matrix then the emission intensity can quantitatively provide the extent of binding between the two, and LIBS may also be able to look into unique molecular signatures by looking at bonds rather than only the elements. Such methods of binding detection for drugs with heavier elements are used in methods developed by X-ray fluorescence (see published US patent application 2005/0011818, which is incorporated herein in its entirety). Unlike X-ray fluorescence LIBS is able to provide information on light elements (e.g., beryllium) and molecular bonds while being less expensive, in part because it does not make use of expensive sources to generate and detect X-rays and the expense needed to shield equipment from the dangerous X-rays. In addition the detection limits of elements by LIBS are superior as compared to X-ray fluorescence. Another related method that can be used is to mix target binders and pharmaceutical chemicals in a reservoir (typically in an aqueous system). These are then put through a separation system such as centrifuges, chromatographs, electrophoretic, capillary-electrophoretic, gel filtration or permeation chromatographs, etc. and the fractions collected in and analyzed in an array using LIBS as is similarly done for methods using X-ray fluorescence in the above cited references. X-ray fluorescence has been used to analyze samples in flow through methods. The method details for LIBS including binding chemistry, and separation are similar as for X-ray fluorescence in US patent application 20050214847 which is included here in entirety by reference herein. US patent applications 20080220441; 20040235059 and 20030027129 discuss detection of binding of biological materials with other materials by X-ray fluorescence (XRF). One of the measurements that is done is to determine therapeutic index, where this and similar measurements are used for estimating drug binding, drug manufacturing and protein modification. The applications and the methods to obtain analytes in these applications are included herein by reference as the same can be used to detect these by LIBS at higher precision, higher safety and lower cost. Further, one can use a variety of substrates and thicknesses to form the arrays as these do not interact in the light as they do by scattering X-rays. Further, the focus of the laser beam can easily be changed from about 20 to 1,200 µm to encompass small or a larger area without a significant change in optics as typically needed for X-rays, and thus, if desired, samples (array-elements) can be made small for dense arrays and matched to the beam size. US patent application 20090046832 describes solutions to measure drug/protein interactions which have typical concentration of these materials of about 100 nanomolar to 10 micromolar. The methods of sample preparation and the applications contemplated in this application are included herein by reference. Since these concentrations are difficult to detect with XRF, they devised an apparatus to concentrate by drying solutions (specific protein/drug pairs are separated into separate solutions as described earlier and arrays of these solutions are formed) in a small area on a plate. Using LIBS methods described above the sample preparation is easier as regular well plates may be used with or without concentration (or drying) and the detection limit and the spatial resolution is typically superior to XRF. However, the array plates mentioned in this method can also be used with LIBS providing the benefits of improved sensitivity at a lower cost. The general concept of a plate to make arrays as shown in the US patent application is reproduced in FIG. 9. This shows the top view of a 96 well plate and a section in front view. The top part of the plate that forms the walls of the wells is shown as 93 and the bottom plate (the bottom plate which may be optionally detachable is shown as 92). A hole at the bottom of each well (so that the solution can touch the bottom plate) is shown as 91. The bottom may be removed after the solutions are dried, or the bottom may not be detachable, and one may have to excite the sample in each well from the top or through the bottom as long as the bottom is transmissive to the radiation. It is not necessary to use conical shape or a fixed volume (cylindrical shape wells or any other shape wells may be used, and the well volumes may vary from several ml to few microliters, and the number of wells on the plate may be any but typically one uses a plate about 8×13 cm with 24, 96, 384 and 1536 wells so that it is easy to handle them using existing automation), as it depends on the degree to which the solutions need to be concentrated to. In this concentration it is important not to loose analyte that sticks to the walls of the well, and it is also preferred that the spot over which it concentrates is even. To achieve this, the solutions that are used should be wetting or have low contact angle with the material used at the bottom of the well and non-wetting or have a high contact angle with the material used for the sides of the well. This means the contact angle of the solution to the walls or sides of the well should be greater than 90 degrees (preferably greater than 120 degrees) and with the bottom it should be less than 90 degrees (preferably less than 30 degrees). For example for an aqueous solution the walls should be non-wetting (hydrophobic) and the bottom should be wetting (hydrophilic). This will ensure that the solution forms an even film as it concentrates at the bottom and does not stick to the sides. In addition, the bottom may be coated with adhesion promoters (e.g., amino silane) or it may also be textured as described earlier (see FIG. 2) so that the solution is divided in many small compartments as it starts to dry. In this case the solution is divided in a number of small volumes so that can dry independent of each other and so that on an average, each compartment has the same amount of material. In this case the size of the texture or the cross section of the small compartments (or each volume) need to be much smaller (less than $1/5^{th}$ or less) than the interrogating beam size For aqueous solutions, some of the materials that result in high contact angles are polyolefins and fluorinated polymers (e.g., polyethylene, polypropylene, polytetrafluoroethylene, fluorinated ethylene propylene polymer and polyvinylidene fluoride), e.g. glass or quartz coated with dichlorodimethyl silane or chlorotrimethyl silane. Some of the hydrophilic materials are nylons (e.g., nylon 6 and nylon 6,6), cellulose acetate, glass or quartz coated with amino silane. For use with aqueous solutions, one may even coat the bottom of the plates with a hydrophilic polymer that may even swell and then dry out uniformly. These coatings may be of crosslinked polymers. Some examples for such coatings are polyacrylamide, polyvinyl alcohol and ionomers such as polystyrene sulfonic acid. In all cases one has to make sure that the composition of the polymer does not interfere with the analysis. For example, if sulfur is key to the analysis then polystyrene sulfonic acid will not be a good choice.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A method to rapidly analyze a number of solid samples to determine the presence of chemical elements of interest, wherein the method comprises a. for each solid sample, extracting the elements or compound of interest from the solid sample into a liquid medium for that solid sample,
b. arranging a number of the said liquid mediums with extracted elements or compounds in an array format, to form array elements,
c. interrogating or exciting the array elements using a laser so as to ablate a fraction of the liquid medium in the said array elements and form a plasma along with a concomitant optical emission from the ablated material,
d. analyzing an optical spectrum produced from the the said optical emission to determine the type and concentration of the presence of the chemical elements of interest, and
e. inferring from this analysis, the type and/or concentration of the chemical elements present in the extracted liquid and or in the samples being analyzed.

2. The method of claim 1, where the said sample comprises at least one of the chemical elements or a compound of an element selected from lead, mercury, cadmium, arsenic, beryllium, thallium, antimony, uranium and selenium.

3. The method of claim 1, wherein the liquids in the array elements are restricted in their flowability by using a thin film of the said liquids or using a medium or an additive within the array elements that is
   a. Porous
   b. Swells in presence of the said liquid
   c. Changes viscosity or forms a gel
   d. Solidifies the liquid.

4. The method of claim 1, wherein the solid samples comprise at least one element of compound comprising any or all of lead, mercury; cadmium, arsenic, beryllium, thallium, antimony, uranium and selenium.

5. The method of claim 1 wherein the liquid in the array elements is increased in viscosity or immobilized prior to subjecting it to laser interrogation.

6. The method of claim 1 wherein the number of array elements are 24, 96, 384 or 1536.

7. The method of claim 1, wherein the array-elements containing the liquid with extracted elements or compound is contained in wells which are sealed at the top using a lid, wherein the said lid iso
   a. permeable to the light of the laser, and/or
   b. the sealed array element is permeable to at least one of the ablation material formed by the interaction of the laser with the liquid in the well, and the optical radiation from the resulting plasma.

8. The method of claim 1, wherein the said method is integrated with robotic sample preparation system and the said robotic system comprises preparing the array automatically.

9. The method of claim 8, wherein the robotic system prepares the array elements in a sequence of processing steps, starting from the samples or starting from the liquids with extracted material from the samples.

10. A method to rapidly analyze a number of liquid samples to determine their chemical elemental composition, wherein such method comprises;
    (a) arranging a number of the said liquid samples as array elements in an array format;
    (b) interrogating or exciting the array elements of the said array using an laser so as to ablate a fraction of the material in the said array and form a plasma along with a concomitant optical emission from the ablated material;
    (c) analyzing an optical spectrum of produced from the said optical emission to determine the type and concentration of the presence of the chemical elements of interest;
    (d) inferring from this analysis, the type and/or concentration of the chemical elements present in the liquid samples.

11. A method to rapidly analyze a number of liquid samples to determine their chemical composition, wherein such method comprises;
    (a) arranging a number of the said liquid samples as array elements in an array format;
    (b) interrogating or exciting the array elements of the said array using a laser so as to ablate a fraction of the material in the said array
    (c) inferring from the analysis of the ablated, material, the type and/or concentration of the chemical elements present in the liquid samples,
wherein the said method is integrated with a robotic sample preparation system and the said robotic system comprises preparing the array automatically.

* * * * *